United States Patent [19]

Joshi et al.

[11] Patent Number: 5,681,435
[45] Date of Patent: Oct. 28, 1997

[54] FLUID DISPENSING PUMP

[75] Inventors: Ashok V. Joshi; John H. Gordon, both of Salt Lake City, Utah

[73] Assignee: Ceramatec, Inc., Salt Lake City, Utah

[21] Appl. No.: 538,439

[22] Filed: Oct. 3, 1995

Related U.S. Application Data

[63] Continuation-in-part of Ser. No. 58,438, May 7, 1993, Pat. No. 5,454,922.

[51] Int. Cl.$^6$ .............................. C25B 1/10; F09B 39/00
[52] U.S. Cl. ................................ 204/266; 204/DIG. 3; 417/437
[58] Field of Search ..................... 204/252, 265, 204/266, 282, DIG. 3; 205/634, 635, 636; 429/163, 164, 169, 170; 417/437

[56] References Cited

U.S. PATENT DOCUMENTS

| | | | |
|---|---|---|---|
| 4,039,409 | 8/1977 | LaConti | 205/631 |
| 4,289,591 | 9/1981 | Davidson | 205/634 |
| 4,568,441 | 2/1986 | Covitch | 204/283 |
| 4,902,278 | 2/1990 | Maget | 604/132 |
| 5,454,922 | 10/1995 | Joshi | 204/265 |

*Primary Examiner*—John Niebling
*Assistant Examiner*—Brendan Mee
*Attorney, Agent, or Firm*—Trask, Britt & Rossa

[57] ABSTRACT

Disclosed is a self-contained device which continuously dispenses a packaged fluid. The device is particularly suited for applications where several months may lapse before performance is manually initiated, after which a consistent steady flow is required for an extended period until the packaged fluid is exhausted. The device is also particularly suited for applications where ease of fabrication and where availability of materials are important factors. A button cell battery provides a driving force to reduce atmospheric oxygen at a simple air cathode, ions are transported through an ion-exchange membrane, and oxygen gas is released at a simple anode. The effective transport of oxygen gas pressurizes a chamber resulting in fluid contained in a flexible bladder within the chamber to be forced through an outlet. This device is intended to be very low in cost and thus disposable.

11 Claims, 5 Drawing Sheets

|  | 0226(03-04) | 0226(05-07) |
|---|---|---|
| ESPI RuO | 21.6% | 27.6% |
| Graphite | 53.3% | 46.6% |
| Nafion | 25.1% | 25.8% |
|  | WET INK | DRY INK |

*Desicated overnight*
*Capillary 1 applied*

FLUID DISPENSING PUMP

RELATED APPLICATIONS

This application is a continuation-in-part of U.S. application Ser. No. 08/058,438, filed May 7, 1993, U.S. Pat. No. 5,454,922, entitled "Fluid Dispensing Pump" pending and commonly assigned. The specification of such prior application is hereby incorporated by reference.

BACKGROUND OF THE INVENTION

1. Field

This invention relates to a dispensing device, in particular, a device where a battery provides the driving force to electrochemically pump oxygen from air into a chamber, and where the pressure increase resulting from the transport of oxygen pushes fluid from a bladder with said chamber through an outlet in a steady, continuous flow until the fluid contents are exhausted.

2. State of the Art

U.S. Pat. No. 3,894,538 disclosed a device for dispensing medicines to man or beast. The medicine was contained in a flexible container which became compressed as fluid was electro-osmotically introduced into an adjacent flexible chamber or when gas was electrolytically produced using precious metal electrodes and an unspecified electrolyte. The rate of medicine discharge was to be regulated using a potentiometer.

Maget in U.S. Pat. No. 4,522,698 disclosed electrochemical prime movers. Embodiments of the invention include a device for dispensing pharmaceuticals to a human body over a substantial period of time at a sustained very low rate, where a battery provides the driving force to transport oxygen from air across an ion-exchange membrane. Pressure in a chamber increases as oxygen transports across the membrane; this increase in pressure drives a piston which forces the contained pharmaceutical fluid to flow through an outlet. The invention requires electrodes which are electrically conductive and act as catalysts to convert molecules to ions; titanium-palladium alloy or palladium black are recommended materials. A controller is utilized to control the magnitude and time pattern of current and voltage applied to the membrane as well as to turn current on and off.

Maget in U.S. Pat. No. 4,886,514 disclosed electrochemically-driven drug dispensers. A potential from an external power source drives an electrochemically-active gas such as hydrogen or oxygen to be transported across a membrane from a fixed volume chamber to a chamber which has a variable volume. The volume of the chamber varies by either flexing an expansible diaphragm-type wall or by displacing a sliding wall, said wall being shared by a second variable volume chamber which contains a fluid drug to be administered. As the electrochemically-active gas is transported to the first variable volume chamber, the drag is forced out of the second variable volume chamber through an outlet. Countering the electrochemical transport of gas across the membrane, the gas diffuses in the opposite direction across the membrane in accordance to the pressure gradient and diffusivity properties of the membrane. A controller compensates for the gas diffusion rate and varies the voltage and current to achieve the desired drug delivery rate in a steady or intermittent mode.

Maget et al. in U.S. Pat. No. 4,902,278 disclosed a fluid delivery micropump. The pump utilizes an air-actuated battery in a fixed closed circuit with an electrochemical cell which drives the transport of oxygen in air across a membrane. The transport applies external pressure to a collapsible reservoir filled with fluid; as a result, fluid is expelled from the reservoir through an outlet. The membrane is preferably a Nafion material (a perfluoro sulfonic polymer) which has been coated with platinum black/10% Teflon. Electrodes are preferably titanium screens. To control the current, a resistor is utilized. The device is activated by removing a protective peel tab to expose air inlet ports to the battery cathode. A disadvantage of this type of system is that shelf life of the device is dependent on the integrity of the seals which prevent air leakage to the battery. If the seals are not perfect, the battery will slowly discharge before the desired time of use.

M. Wilson and S. Gottesfeld have described in articles entitled "High Performance Catalyzed Membranes of Ultra-Low Pt Loadings for Polymer Electrolytic Fuel Cells," and "Thin-Film Catalyst Layers for Polymer Electrolyte Fuel Cell Electrodes" published, respectively in, J. Electrochem, Soc. Vol. 139 no. 2, February 1992, 628–630, and Journal of Applied Electrochemistry 22 (1922) 1–7, two methods for applying thin film catalytic electrodes to cationic membranes. In each case, a mixture of Pt and C are utilized as the catalyst and electronic conductors while solubilized Nafion (from duPont) is used as the binder and ionic conductor for the electrodes. The electrodes were designed for and tested in fuel cell applications. While such an electrode is excellent for an oxygen-reducing cathode, it is unsatisfactory for an oxygen evolving anode since current density decays considerably in a short time.

J. Ahn and R. Holze, in "Bifunctional electrodes for an integrated water-electrolysis and hydrogen-oxygen fuel cell with a solid polymer electrolyte," published in J. of Applied Electrochemistry Vol. 22 (1992) pp. 1167–1173, present data where Ru-oxide, Ir/Ru-oxide, Ir-oxide, Ir, Rh-oxide, Rh, Pt and Rh/Ru-oxide were utilized as catalysts for oxygen evolving electrodes. Of these catalysts, Pt was one of the worst catalyst. Ru-oxide, Ir/Ru-oxide, Ir-oxide and Ir were the better catalysts. Ahn and Holze, in their study, mixed these various catalysts powders with 10% PTFE and formed porous layers which were pressed on to Nafion membranes.

K. V. Ramesh, P. R. Sarode, S. Vasudevan, and A. K. Shukla in "preparation and characterization of carbon-based fuel-cell electrodes with platinum-group bimetallic catalysts," J. Electroanal. Chem., 223 (1987) 91–106 present data indicating that 4% Pt+6% Ru dispersed on activated carbon forms an elctrocatalyst/electroconductor which is superior to either Pt or Ru catalysts for the reduction of oxygen in a fuel cell application. Ramesh et. al. also describe a procedure for dispensing the Pt/Ru alloy on activated carbon by reducing a solution of chloroplast acid and ruthenium chloride in the presence of the activated carbon.

Tuck describes in *Modern Battery Technology*, Ellis Horwood Ltd. (publisher) 1991, pp. 125–160, the hardware components commonly used in vast quantities in the small-battery industry. Utilization of such components for different kinds of devices is unknown.

The prior art includes several devices which are capable of performing the general function of the device presently disclosed. Thermal units, using an electrical resistor as a heat source, are made to dispense fragrances within a room. These units consume considerable power and plug into a typical 110v house outlet. These units are not portable and do not dispense the volatile fragrances at a constant rate.

Thus, the prior art has not satisfied a demand which exists for a device which 1) has a design which can dispense a fluid over a nearly constant rate for an extended period of time, 2) has a simple design which is conducive to fabrication, 3) has a design which minimizes the use of materials which are not readily available, and 4) which is small in size and portable, i.e. battery powered. The present invention especially offers advantages relating to the last two factors, which until now have precluded the widespread use of the prior art in disposable consumer products.

SUMMARY OF THE INVENTION

A fluid-dispensing, electrochemical pump, especially a micropump, has been invented. The pump utilizes an electrochemical cell having a thin-walled, substantially non-porous polymeric ionomer, such as polyperfluoro-sulfonated ethylene, which has one ionic/electronic conducting electrode capable of reducing oxygen in the presence of watts or protons and another electronic/ionic conducting electrode suitable for oxygen evolution. Oxygen produced by the electrochemical cell is discharged into a gas-tight chamber containing a fluid-filled bladder whereby fluid is dispensed from said bladder at a rate substantially equivalent to the oxygen discharge rate of said electrochemical cell.

The invention provides a self-powered, low-cost, fluid-containing, electrochemical device which has a long shelf life and which dispenses the fluid at a slow, steady rate over an extended period of time. While inventions disclosed in the prior art were generally intended to deliver medicines of some kind; the instant invention will deliver various liquid substances which would impart a benefit when dispensed. The fluid, which is generally a liquid, may contain chemicals or nutrients which provide a benefit or which inhibit something undesirable. The fluid could be delivered to a specific site through appropriate tubing and connections, for example, a delivered volatile liquid could be allowed to evaporate into a particular space, such as a room, vehicle, container or other environment surrounding the dispenser. The dispenser, especially in miniature form, could be embodied in a form intended to be stationary, sitting upon something or hung from something, or it could be embodied in a form to be worn on a person in the form of a pendant, or in a form to be worn on a person's clothing, or in a form to be worn on an animal in the form of a collar, or in a form to be hung from a tree or other type of plant.

The present electrochemical device is delivered to consumers in a disabled, i.e. non-operable, condition so that no drain on the battery or premature activity occurs when the device is on the shelf, waiting to be used. Activation occurs when the consumer completes an electric circuit by snapping electronically-conducting components of the device together or by removing a temporary insulator from between two electronic contacts. In addition, the user typically unseals the fluid sack outlet by removing a plug, or by cutting or puncturing a sealing membrane. Thus, neither the power supply nor the fluid contents will be compromised before the device is to be utilized.

A button cell battery which is low in cost, efficient and readily available provides the driving force for the device. Oxygen from air is the working substance. The battery provides a potential difference between electrodes on each side of an ion-exchange membrane. Oxygen is effectively transported across the membrane electrochemically. The oxygen is transported to a gas-tight chamber which encloses a flexible bladder containing the fluid to be dispensed. As oxygen is transported into the gas-tight chamber, the resulting increase in pressure compresses the bladder such that the fluid flows through an outlet to the desired destination or to a site on the dispenser where the fluid can evaporate.

The rate of fluid dispensing is directly proportional to the rate of oxygen transport which is directly proportional to the electrical current. The electrical current required to dispense the fluid is very low, about 183 $\mu A$ per ml fluid per day at standard conditions. To determine actual fluid delivery at conditions other than standard, the following relationship can be used:

ml actual per day=$0.014 \times C \times T/P$;

where:

$C$=Current in $\mu A$,
$T$=Temperature in degrees K.
$P$=Pressure in Torr

Many applications involving concentrated chemicals will require substantially less than 1 ml per day to be effective, thus total current flow in the range 5 $\mu a$–500 ma would be typical for this device although the device is not limited to this range. Such a current range would provide fluid delivery ranges from 0.3 ml per day to 100 ml per hour.

A cation exchange membrane (ionomer) in the protonic form is preferably utilized in the device. Transport of oxygen through the membrane is achieved through the following reactions:

Cathodic reaction: 
$O_2 + 4H^+ + 4e^- \rightarrow 2H_2O$

Anodic reaction: 
$2H_2O \rightarrow O_2 + 4H^+ + 4e^-$

Protons migrate through the membrane under the influence of a potential gradient, and unless water is supplied at the anode, moisture must diffuse through the membrane to sustain the process. Membranes should be in the protonic form, which can be achieved by lightly boiling the membrane in 0.1M sulfuric acid for two hours then rinsing in deionized water. To maintain steady and repeatable performance of the device, maintaining a consistent level of membrane hydration is desirable. Two strategies are possible: 1) maintain full hydration by incorporation of a moisture reservoir on the anode side or 2) allow the membrane to equilibrate with the moisture in the atmosphere before activating.

The cation-exchange membrane Nafion (by duPont) has been found to be particularly satisfactory in this invention. Wilson and Gottesfeld have worked with "C" membrane (by Chlorine Engineers of Japan) in fuel cell applications with results comparable to Nafion, thus "C" membrane is expected to also be satisfactory for this device.

The preferred membrane, perfluoro-sulfonated ionomer, is marketed as Nafion by duPont. Other useful membranes include pufluorcarboxylated ionomers, polyethylene sulfonated ionomers, polyethylene carboxylated ionomers and the like. These materials are referred to as "ionomers" inasmuch as they are polymers which transport an ion, which, for the above-identified ionomers, is a proton ($H^+$).

The references cited above by Wilson and Gottesfeld describe two methods by which electrodes may be attached to the membrane. The method described in "Thin-film catalyst layers for polymer electrolyte fuel cell electrodes" is preferred because of the ease of fabrication. An ink is made from an electrocatalyst, an electronic conductor, solubilized ionomer (5% Nafion from Solution Technologies), water and glycerol. The ink is painted, or droppered onto the membrane and dried in an oven, resulting in an electrode which is both electronically and ionically conductive and is intimate with the membrane; however, the electrocatalyst and electronic conductors utilized by Wilson and Gottesfeld for their application, namely Pt on C (Vulcan carbon black) are unsuitable for an acidic oxygen evolving electrode such as that required in the instant invention. Performance of cells with such a Pt/c anode decay considerably in a matter of days.

A combination of 10–90 Ru-oxide and 10–60% ionomer (all on a dry basis) with balance C (Asbury graphite #5645) or Ebonex (a conductive $Ti_4O_7$ material by Ebonex Technologies) have been found to be excellent materials for the anode of this invention, providing performance without decay. Also, these materials perform adequately as cathodes and are more readily available than Pt on C as utilized by Wilson and Gottesfeld. Ir/Ru-oxide, Ir-oxide, and Ir according to Ahn and Holze, are suitable as oxygen evolving electrocatalysts, however, these materials are less readily available compared to Ru-oxide.

Without complicating the present invention, four strategies can be taken to make adjustments such that devices with the desired substance dispensing rate are achieved. 1) The area of active membrane surface can be made larger or smaller. Increasing electrode area increases current and hence fluid dispensing rate. 2) The concentration of the desired substance in the fluid can be changed. Thus, without changing the flow rate of the fluid, the flow rate of the desired substance can be increased or decreased by increasing or decreasing the concentration of the substance in the fluid dispensed. 3) Changing the ratios of electrocatalyst/electronic conductor/ionomer in the electrode ink affect the current density at a given potential in the device. Also the selection of electrocatalyst and electronic conductor to be utilized affect the current density. 4) The ionomers are available in different thicknesses; current density is increased as thinner membranes are used in the device. These strategies can be taken during manufacture to customize devices to meet the requirements of particular applications.

To ease fabrication, components which are readily available from the small-battery industry, namely the can, sealing grommet, and cap may be readily utilized in this device.

Advantages and clarification of the invention will become apparent from the drawings and more detailed description below.

DETAILED DESCRIPTION OF THE PREFERRED EMBODIMENTS

Figure 1:
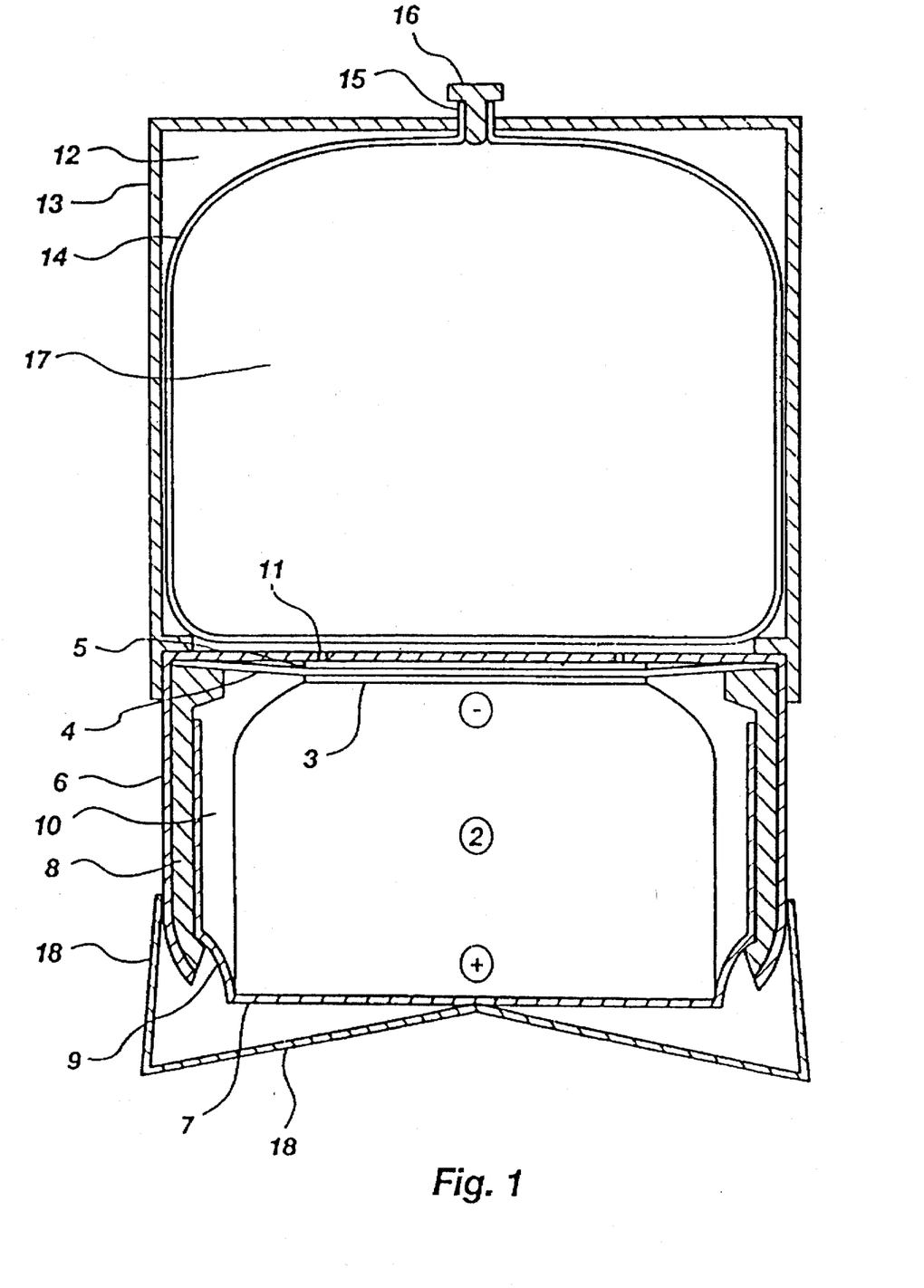
FIG. 1 is a perspective sectional view of a fluid dispensing micropump embodying features of the present invention.

For purposes of illustration of the present invention, an embodiment of the fluid dispensing micropump is shown in FIG. 1. The pump shown is circular in shape which improves the ease of fabrication; however, other shapes such as a square, rectangular, triangular, etc. are also possible and may be desired for aesthetic reasons or to facilitate incorporation into another structure. The pump is integrally powered by a button cell battery 2 which is readily available at low cost. The negative pole of said battery directly contacts the oxygen reducing cathode 3. Adjacent to said cathode 3 is the ionomeric electrolyte 4 which, as mentioned above, is preferably a nonporous, cation-exchange membrane. Adjacent to said membrane, opposite said cathode, is the oxygen evolving anode 5. Intimate contact between the electrodes and the membrane is required to ensure reproducible performance of the device. A convenient method to achieve this goal is described above and in the references by Wilson and Gottesfeld cited above.

The pump shell 6 acts as a current collector and supporter of the anode. Said pump shell may be either an electronic conductor or a plastic which has been coated with an electronic conductor on the surface in contact with the anode. A convenient embodiment of the pump shell are the AR41, AR44, AR48 "positive cans" commercially used for a zinc-air battery. These are readily available from Taiei Sales & Eng. or Power Eng. Also convenient for the pump shell are the SR43, SR44, SR54, SR55, and SR57 "positive cans" for alkaline batteries which are readily available from the same manufacturers. Many of the manufacturers of these components are listed by Tuck in Modern Battery Technology.

Similarly, the "negative tops" and "grommet seals" for the above-mentioned zinc-air or alkaline batteries can be utilized for the cap 7 and grommet 8. Said cap is crimped in a way such that it centers the button cell 2. Said grommet is made from a pliable electronic insulator such as nylon. The grommet electrically insulates the cap from the pump shell. The pump shell, grommet and cap are crimped to cause the grommet to press against the ionomer, thus sealing the perimeter of the ionomer to the pump shell. In addition, the crimp presses said button cell against said cathode.

Air inlets 9 allow oxygen to enter and nitrogen to exit out of the air passage 10. Oxygen outlets 11 allow oxygen evolving from the anode 5 to enter the oxygen cavity 12 which is enclosed by the oxygen shell 13. Said oxygen shell is attached and sealed to said pump shell 6.

Within the oxygen cavity is a fluid sack or bladder 14 which contains the fluid to be dispersed 17. Said fluid sack is made of a flexible material which has adequate corrosion properties for said fluid. Said fluid sack has an outlet 15 which passes through said oxygen shell and is sealed thereto by gluing or other means. Said fluid sack outlet may be very simple or may have a fitting for the attachment of tubing, or may have an attachment suitable for promoting evaporation of the fluid, e.g. volatile liquid, into the surrounding air. Said fluid sack may be sealed from the external environment before the time of activation with a plug 16, clip or other means or may have a sealed portion which protrudes through said outlet which is cut off or punctured by the user at the time of activation.

The user activates the device by utilizing a contact clip 18 to complete circuit between the pump shell 6 and the cap 7. Once the circuit is completed, oxygen is pumped into the oxygen cavity, exerting pressure on said fluid sack and forcing said fluid through said opening as the device operates.

Figure 2:
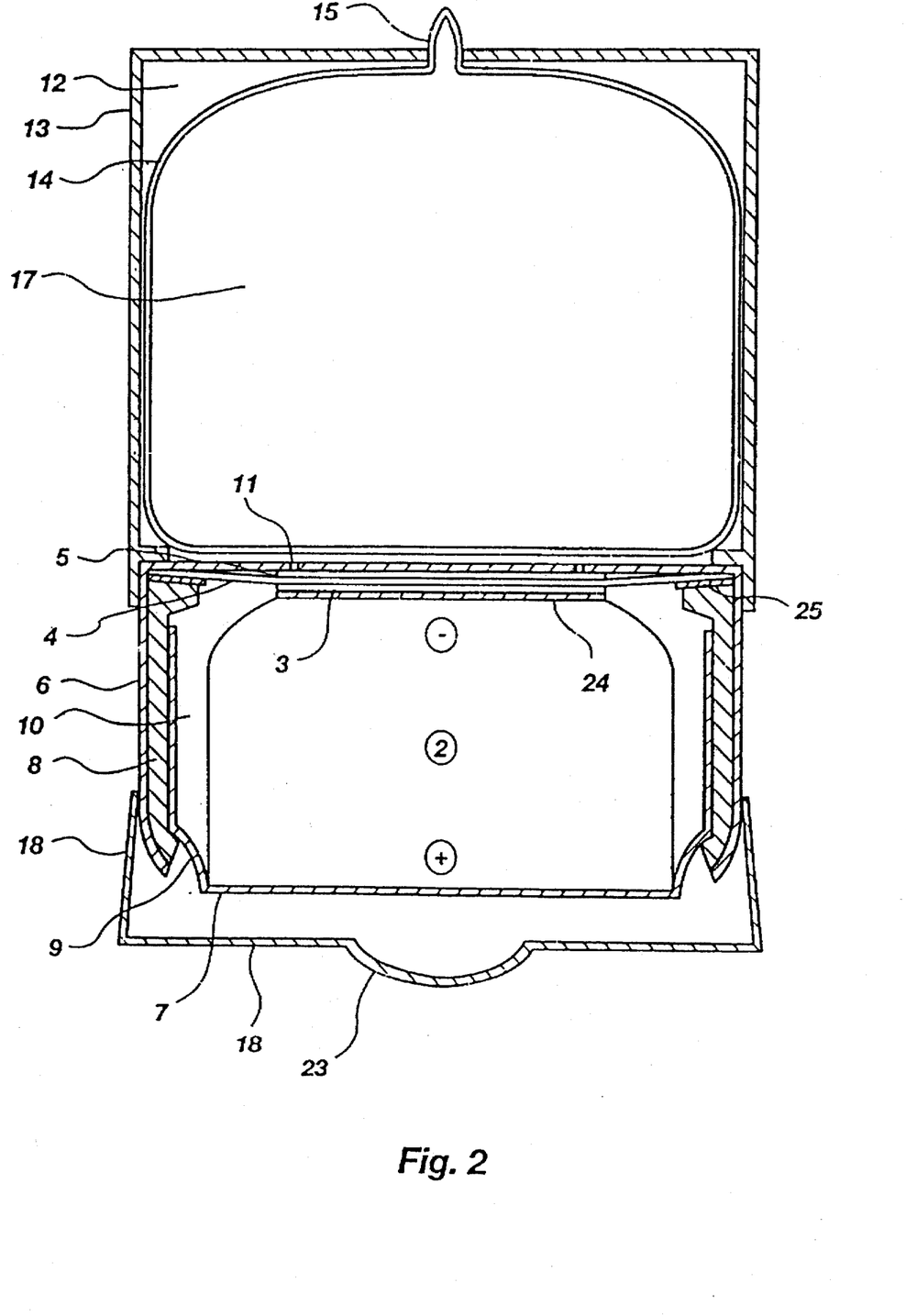
FIG. 2 shows a perspective sectional view of an embodiment of the invention which is a variation of what was shown in FIG. 1.

FIG. 2 shows a perspective sectional view of an embodiment of the invention which is a variation of what was shown in FIG. 1. In this case, the contact clip 18 has been varied. The said contact clip is assembled in contact with the pump shell 6. The user activates the pump by pressing on tab 23. Said tab inverts position (dotted line position 23') such that contact with the cap 7 is achieved. This figure shows the embodiment where the fluid sack 14 is sealed at the outlet 15 by a bladder protrusion 30 of which the end is to be cut off or punctured by the user at the time of activation. This embodiment further shows a porous, electronically-conductive mesh 24 situated between the button cell 2 and the cathode 3. This enables the pumping rate to be increased by enabling higher mass transport of oxygen to the cathode. Also shown in this embodiment is a gasket 25 which may be utilized to enable sealing of the ionomer 4 to the pump shell 6 in the case where standard, readily available components 2, 6, 7, and 8 do not fit together perfectly.

Figure 3:
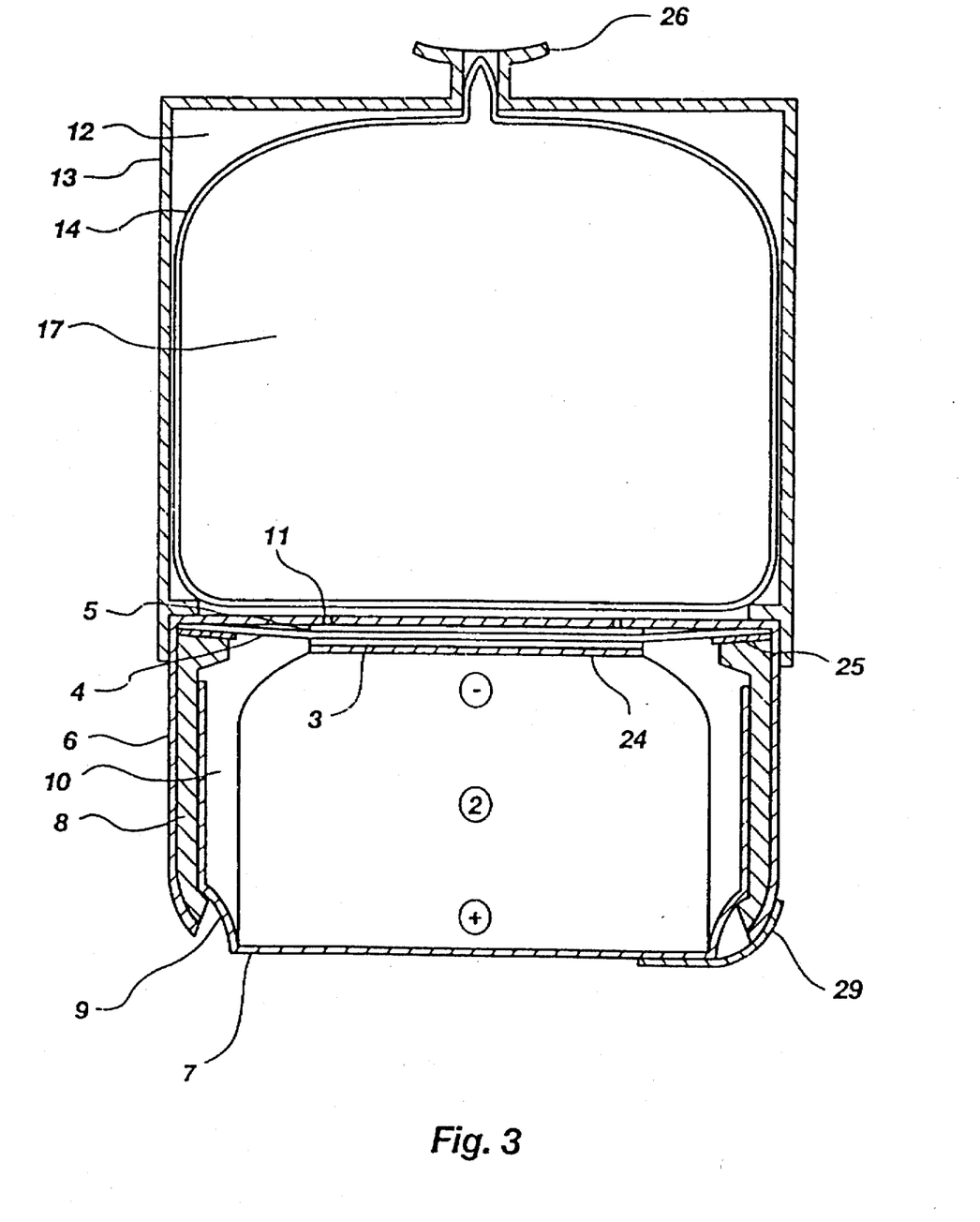
FIG. 3 shows perspective sectional view of another embodiment of the device.

FIG. 3 shows a perspective sectional view of another embodiment of the device. Many features are similar to those shown in FIG. 1 and are numbered similarly. Here the contact clip is eliminated and a piece of electronically-conductive tape 29 is applied by the user to complete the circuit at the time of activation. Also shown is an evaporation fixture or pan 26 which would temporarily hold dispensed fluid (after puncturing bladder protrusion 30) until it evaporates.

Other structures of micropumps incorporating the invention may be made. The preferred embodiment described hereinabove is especially useful because of its small size, generally having a diameter and thickness less than one-half inch. Such a unit is self-contained, storage-stable and reliable in operation. The particular structure described lends itself to enable easy cell activation. Once activated, the electrical contacts are reliable and the desired oxygen generation ensured.

Figure 4:
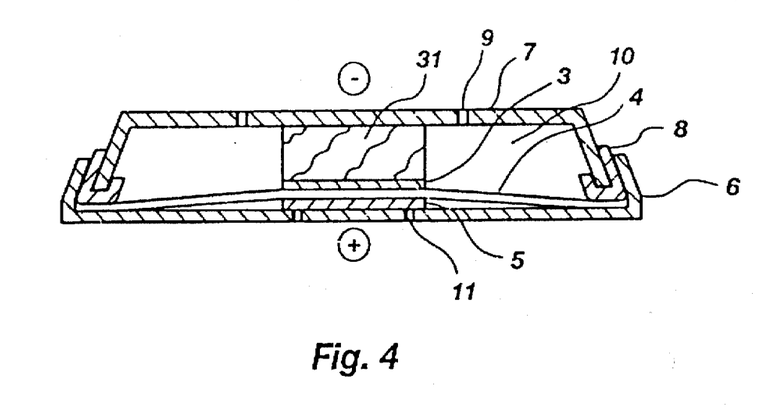
FIG. 4 is a schematic view of a pump structure to be powered by an external source such as a solar cell, rechargeable battery of rectified AC source.

FIG. 4 shows a perspective sectional view of an embodiment of the invention. Only a portion of the pump is shown. In this embodiment, a battery is not incorporated so that an alternative DC power supply such as a solar cell, rechargeable battery, or rectified AC supply can be utilized to power the pump. The pump shell 6 and cathode cap 7 and grommet 8 have the shape and configuration of "coin" type lithium batteries so these parts are readily available. The oxygen reducing cathode 3, ionomer 4, oxygen evolving anode 5, air inlet 9, air passage 10, and oxygen outlets 11 serve the same functions as in the embodiments shown in FIGS. 1–3. The negative lead of the DC power supply is contacted anywhere on the cathode cap 7. An electronically conducting spacer 31 which may be mesh, porous, or solid material provides electrical continuity to the cathode 3. A battery, of course, could be substituted for spacer 31. The positive lead of the DC power supply is contacted anywhere on the pump shell 6.

The mechanical structure of the instant invention is particularly well-suited for low-cost, efficient assembly. The pump housing is a small, thin-walled, electroconductive metallic cylindrical "can" having a closed end, with small apertures, and an open end. The anode/electrolyte/cathode assembly may be independently formed and inserted, anode side down. A cylindrical grommet is inserted which is form-fit to the inside of the can to hold the electrolyte membrane in place. A button-cell battery is inserted, oriented so that the negative pole contacts the cathode of the membrane assembly. Another "can" is inverted and inserted inside the grommet. This second "can" has one or more apertures in it and serves to hold the battery in place. The external can (pump housing) is crimped at its open end to hold the battery, retaining "can" and grommet in place.

This efficiently manufactured micropump may be secured to a bladder-containing chamber, which may be metal, plastic or other structure.

The micropump may be assembled into an apparatus such as that illustrated in FIG. 1 or it may be inserted in a mold and have a plastic material injected about it to form a bladder-holding chamber.

The miniature pump may be fitted with various types of electrocontacts which generally create a permanent electrical connection from the anode of the electrolyte assembly to the anode (positive pole) of the battery. Such contacts are illustrated and described with reference to the attached drawings.

Figure 7:
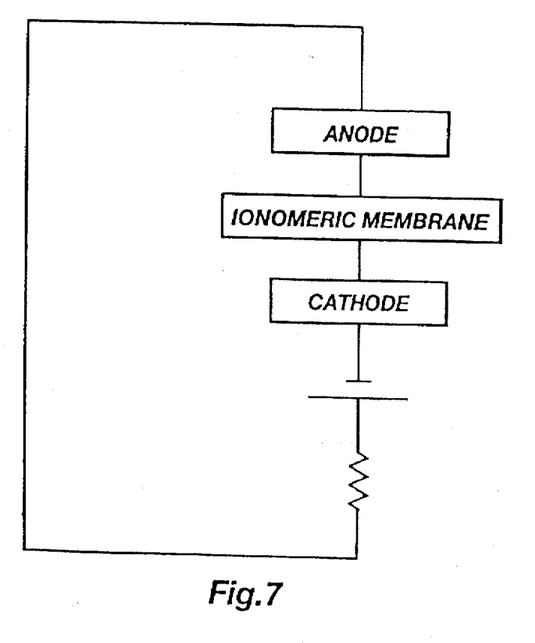
FIG. 7 is an electrical schematic of the instant invention.

FIG. 7 is an electrical schematic of the instant invention. The anode is of a composition prepared as described herein. Its dimensions are typically but not limited to a thickness of 0.00025 to 0.0025 cm and an area of 0.05 to 2 $cm^2$.

The electrolyte has a thickness of about 0.005 cm to about 0.018 cm and a conductivity of about 0.01 to about 0.07 $(\Omega\text{-cm})^{-1}$.

The cathode is of a composition prepared in the manner set forth herein. Its dimensions are typically, but not limited to, a thickness of 0.00025 to 0.0025 and an area of 0.05 to 2 $cm^2$.

Preferred dimensions may range up to 3 $cm^2$ for anode, cathode and electrolyte.

The preferred batteries are those having a voltage output of one to three volts (D.C.), especially alkaline batteries, having a power output of 30 to 200 milliamp-hour, which typically powers the micropump of the instant invention for about 1 to 100 days.

The resistor shown, if used, may have a resistance of about zero to 20,000 ohms. The resistor may be included to control the rate of oxygen evolution, thereby controlling the pumping rate.

The actual voltage drop across the electrodes and the interface between electrodes and electrolyte are often difficult to predict, and may vary somewhat as environmental factors such as humidity and temperature change. Thus, the inclusion of a resistor having a large resistance in comparison to the electrode/electrolyte/electrode assembly can give a more predictable $O_2$ output.

Microbatteries of various types may be utilized, however, the ones described above were chosen because of their minute size and constant reliable power output. Also, these preferred batteries do not degrade significantly upon storage. This is especially important for devices being sold at retail, e.g. fragrance pumps, wherein the device must work reliably and predictably even after setting upon a store shelf for months.

The preferred embodiment illustrated herein has a structure especially suited for a fragrance dispensing device. The structure may be readily manufactured and assembled; stored for long periods without degrading and readily and easily activated to perform reliably.

Since the instant micropump is battery powered, it may be used virtually in any environment. When combined with a fluid dispensing reservoir it could be worn by a human or an animal or it could be activated and surgically implanted in a human or an animal if a volume of oxygen or air is supplied to the cathode.

The pump may be used for dispensing minute quantities of oxygen for numerous purposes besides being a fluid dispensing pump. For example, in a sealed environment such a micropump could dispense predetermined flow rates of oxygen to an aerobic biological system, e.g. a sealed biological system in which predetermined quantities or flow rates of oxygen were required or desired.

The device of the instant invention is especially suitable for dispensing volatile liquid fragrances. The oxygen micropump produces a slow, steady flow of oxygen to displace microliters per day of the fragrance. Even at room temperature, the rate of evaporation of the fragrance is such that the liquid fragrance evaporates substantially as fast as it is "pumped" from its flexible sack to an external location.

Liquids other than fragrances, such as insecticides, deodorizers, nutrients, pharmaceuticals and the like, of course, may be delivered in a steady, controllable, flow rate. The pump can be sized and structured to deliver predetermined volume flows of liquids via the predictable flow rate of oxygen for a pump of a certain size, materials of construction and imposed voltage. Alternatively, the micropump may be constructed as a large apparatus to pump milliliters or even liters per day of oxygen or fluid.

The membrane material preferred in the instant invention is a polymeric material which conducts protons. One such material is marketed by duPont under the identification "Nafion." Sulfonated perfluoro polymers are particularly useful for the purposes of this invention.

The general structure of the perfluoro sulfonated ionomer, namely Nafion, utilized in this invention is:

Pretreatment of the Nafion for the purposes of this invention is relatively standard. The electrodes are prepared by a procedure which was largely adopted from "High Performance Catalyzed Membranes of Ultra-low Pt Loadings for Polymer Electrolyte Fuel Cells" by Mahlon Wilson and Shimshon Gottesfeld. It differs significantly from Wilson and Gottesfeld in the electrocatalyst and application. Theirs is a fuel cell application where no oxygen is evolved at the anode. For this invention, it has been found that Pt, to be acceptable for the purposes of this invention in our application of oxygen pumping, as a catalyst only at the cathode. If Pt is used at the anode, current density drops dramatically within days. This disadvantage is not observed when Ru-oxide is the electro-catalyst at the anode.

Acceptable electrode concentration ranges:

| Nafion | 05%–35% |
| Ru-oxide | 05%–85% |
| Carbon or Graphite | 00%–80% |

Preferred electrode concentration ranges:

| Nafion | 10%–60% |
| Ru-oxide | 5%–80% |
| Carbon or Graphite | 0%–80% |

Especially preferred ranges are:

| Nafion | 20%–35% |
| Ru-oxide | 20%–50% |
| Carbon or Graphite | 15%–60% |

These compositions may be used at either electrode although the cathode may be constructed with platinum. Acceptable results occur at 15% $RuO_2$ levels. While $RuO_2$ may be used at high levels, quantities above about 30% by weight do not appear to contribute significantly to increased catalytic activity.

Ir, Ir-oxide, or Ir/Ru-oxide may be substituted for Ru-oxide and allow higher current density when used in the anode rather than Ru-oxide. Also Pt, or Pt/Ru or Ru dispersed on carbon as described by Ramesh et at. may be substituted for Ru-oxide in the cathode; however, these other electrocatalysts are less readily available. Advantages of electrodes of the instant invention in comparison to those of Maget's are the following:

1) Lower cost materials
2) Fewer process steps
3) Lower contact resistance
4) Less stress on the membrane when applying Other useful membranes which are similar to Nafion may be used. Such membranes are "C" membrane by Chlorine Engineers. Dow is also developing a membrane called XUS-13204.10 which is similar to Nafion.

OXYGEN MICROPUMP ELECTRODE APPLICATION PROCEDURE

1 Membrane Preparation

To prevent deterioration of the membrane in the subsequent drying step, the membrane must be converted from the protonic form to the sodium form.

1.1 Soak membrane in lightly boiling 0.1% NaOH solution for 2 hours.
    1.2 Rinse membrane in deionized water.
    1.3 Air dry membrane for 24+hours.

2 Ink Preparation

Materials

Electro-catalyst: Ru-oxide, Ir-oxide, Ir, Ir/Ru-oxide for anode or cathode. B-black, Pt/Ru or Ru dispersed on carbon, can be used as cathode, not as anode. Pt, Pt/Ru or Ru may improve current density when used as cathode.

Electro-conductor: Graphite, $Ti_4O_7$, Ti, Carbon black     Solubilized membrane (in alcohols and water)

Glycerol

Deionized water

NaOH solution

2.1 Pre-mix deionized water and glycerol in a 1:4 weight ratio, store mixture in a container. Set aside.
    2.2 Weigh appropriate mounts of electro-catalyst and electro-conductor materials into a clean container.
    2.3 Weigh an appropriate mount of solubilized membrane and add to materials in step 2.2. Mix.
        Note: Typically add 1 part solubilized membrane (on a dry membrane basis) to 3 parts electrocatalyst/electroconductor mixture.
    2.4 Weigh and add an appropriate mount of water/glycerol mixture to mixture in step 2.3. Mix.
        Note: Typically add 25 parts water/glycerol mixture to 1 part electrocatalyst/electroconductor mixture.
    2.5 Weigh and add an appropriate mount of NaOH solution to the mixture in step 2.4. Mix.
        Note: Enough NaOH must be added to the mixture to neutralize any protons in the solubilized membrane. If the solubilized membrane is already in the $Na^+$ form, then step 2.5 may be omitted. (For 5% Nafion solution from Solutions Technology, add 1N NaOH in a 1:10 ratio, 1N NaOH to Nafion solution.)
    2.6 Further mix ink ultrasonically for at least 30 minutes.

3 Electrode Application/Drying

3.1 Re-mix ink ultrasonically for at least 30 minutes prior to use.
    3.2 Dip capillary into ink and cap end, or fill dispensing machine tubing with ink.
        Note: Capillary or dispensing machine tubing OD will determine diameter of electrode. The latter will be larger.

3.3 Contact the capillary or dispensing machine tubing to the surface of the membrane at the desired location. Contact will cause a reproducible amount of ink to leave the capillary.

3.4 Place the membrane with wet electrode in an oven at 70°–90° C. for 30 minutes then at 175° C. for 30 minutes.

3.5 Repeat the above steps on the opposite side of the membrane.

4 Acidification 4.1 Soak membrane/electrodes in lightly boiling 0.1% M $H_2SO_4$ for 2 hours.

4.2 Rinse membrane/electrodes in deionized water.

4.3 Air dry membrane/electrodes.

The membrane should be air dried for several days, or air dried then desiccated overnight, or placed in a 50° C. oven for 2 hours before cutting to final dimensions.

Figure 5:
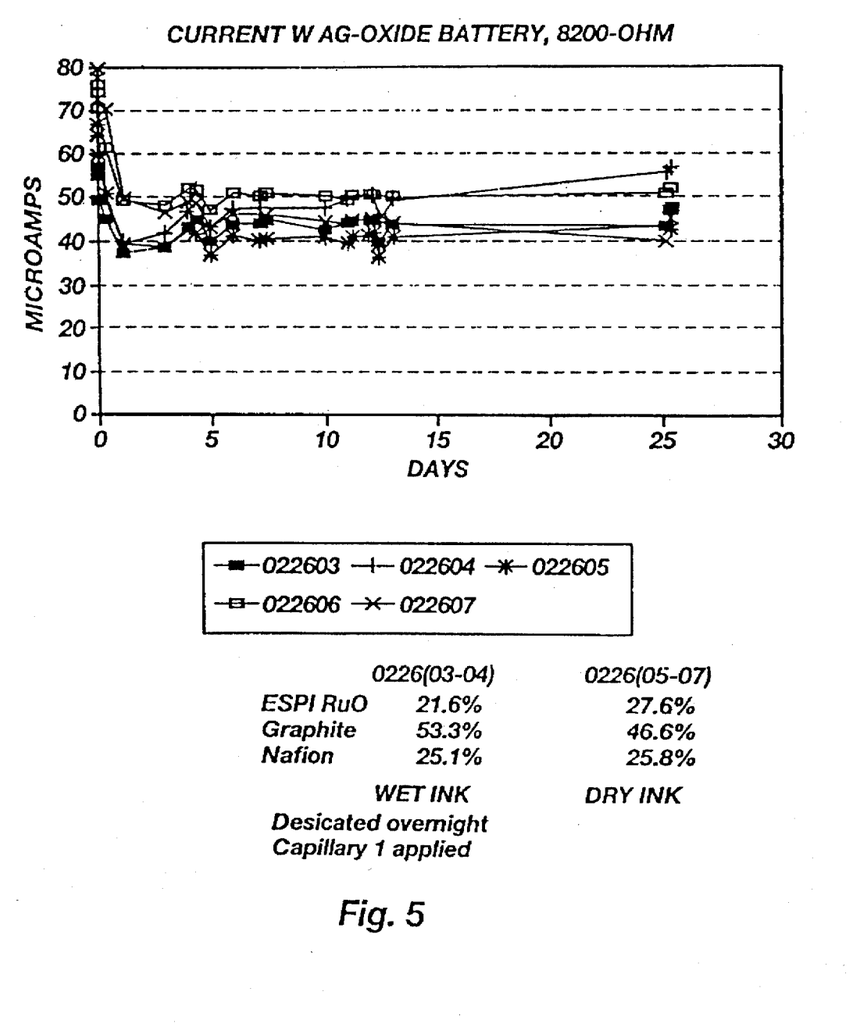
FIG. 5 is a chart indicating current output of an electrochemical cell of the instant invention.

Attached FIG. 5, "CURRENT w AG-OXIDE BATTERY, 8200-OHM," shows the current passing through an oxygen pump over a period of 25 days. The rate of oxygen pumped was directly proportional to the current over the period. Note that after a short charging period, the current remained virtually constant over the testing period. Both anode and cathode consisted of the components listed at the bottom of the figure. A Nafion 115 membrane was utilized for the ionomer. An Eveready 393 button cell was utilized to drive the pump.

Figure 6:
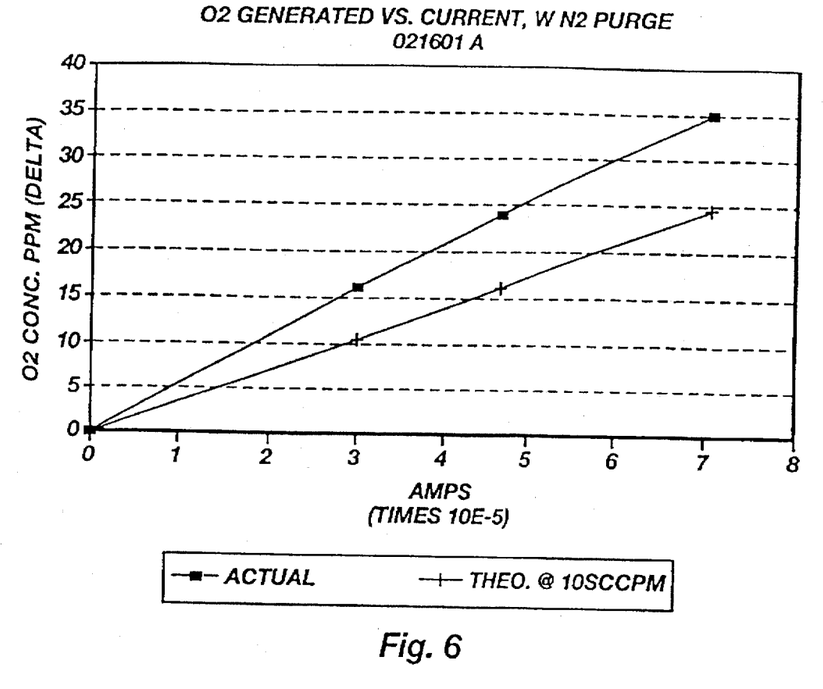
FIG. 6 is a chart indicating oxygen generation of an electrochemical cell of this invention.

Attached FIG. 6, "$O_2$ Generated vs. Current, w $N_2$ Purge," shows the results of a test which demonstrated the direct relationship between oxygen pumped through one of the pumps described in this invention versus the current which passed through the cell. An oxygen pump was placed in a fixture such that air was exposed to the air inlet ports while the oxygen outer ports fed into a piping system which was sealed from air. Approximately 10 scc per minute of $N_2$ gas was flowed across the pump's oxygen outlet ports then subsequently flowed to an highly sensitive oxygen sensor. The pump was activated with a variable resistor in the circuit. The background oxygen concentration was subtracted from the oxygen concentration measured as a function of current passing through the pump circuit. This delta oxygen concentration plotted versus current is shown in the figure. Note that the curve is linear. Also shown is the theoretical oxygen concentration versus current expected assuming that the $N_2$ gas flow was exactly 10 scc per minute. The difference between the actual and theoretical curves can be explained by an actual $N_2$ flow during the test which was somewhat lower than 10 scc per minute.

The use of a micropump of the type described herein to pump volatile liquid fragrance into a space external to said pump requires that the pumping rate be substantially equivalent to the evaporation rate at about room temperature from its discharge opening. A pumping rate faster than said evaporation rate will result in the "leaking" of liquid from the device. The pumping rate may be less than the evaporation rate of said volatile liquid, which results in the pumping rate being the controlling rate for the discharge of vapors of said volatile liquid fragrance.

The area of the discharge opening and the relatively volatility of said liquid will determine the evaporation rate at the discharge opening.

The matching of evaporation rate and pumping rate is not a criterion which must be met in drag delivery devices, for example, where a liquid is delivered as such, i.e. no phase changes. Construction of a delivery device for fragrances must meet a number of criteria, such as minute size, a pumping life of 30–90 days, simple construction, simple and readily available materials.

The uses to which the instant invention may be put are varied. The size of the devices may vary considerably to suit a particular use. Generally, however, these devices are very small and deliver micro volumes of gas to deliver microliters of liquids at predictable, substantially constant rates over extended periods of time.

The unique combination of electrode and structural members enable the devices of the instant invention to be easily assembled to form reliable devices.

Other devices and embodiments are within the scope of the invention. For example, the cell illustrated in FIG. 4 utilizes a separate battery as the power supply. The cell, however, may be constructed as a gas-generating, galvanic cell and, thus, not require a separate power supply.

What is claimed is:

1. A disposable micropump for delivering volatile liquids to a space external to said pump comprises:

a micro battery power supply having a voltage output of about 1 to 2 volts; a power output of about 30 to 200 ma-hr over a period of time of about 10 to about 180 days, said battery having a negative pole and a positive pole;

a non-porous, solid electrolytic ionomeric membrane capable of transporting protons and diffusing water, said membrane having a thickness of about 0.005 cm to about 0.018 cm and an area of about 0.5 to about 3 $cm^2$;

a first electronic and ionic-conducting electrode containing an oxygen-reducing catalyst which reduces oxygen in the presence of water, said electrode containing an ionomeric binder, said electrode being formed on one surface of said membrane and having an area which is less than said electrolyte;

a second electronic and ionic-conducting electrode bonded to said membrane on a surface opposed to said first electrode, said second electrode having an area substantially the same as said first electrode.

2. The disposable micropump of claim 1, wherein said first electrode has a composition of 5–85% Ru-oxide, 15–35% perfluoro-sulfonated ionomer, and 0–80% graphite or carbon powder.

3. The disposable micropump of claim 1, wherein said second electrode has a composition of 5–85% Ru-oxide, 15–35% perfluoro-sulfonated ionomer, and 0–80% graphite or carbon.

4. The disposable micropump of claim 1, wherein said battery is connected electrically to said electrode via a resistor having a resistance of about 2,000 Ω to about 20,000 Ω.

5. The disposable micropump of claim 1, wherein said pump delivers said volatile liquid to its discharge opening at a rate which is substantially equivalent to the evaporation rate of said liquid from its discharge opening.

6. The pump of claim 1, wherein said first electrode has a composition of about 5–20% Ru.

7. The disposable micropump of claim 1, wherein said first electrode has a composition of about 5–85% Ru, 15–35% perfluoro-sulfonated ionomer and 0–80% graphite or carbon powder.

8. The pump of claim 1, wherein said second electrode has a composition which is about 5–15% Ir alloy.

9. The disposable micropump of claim 1, wherein said second electrode has a composition of 5–85% Ru/Ir alloy, 15–35 of perfluoro-sulfonated ionomer and 0–80% graphite or carbon.

10. The improvement of claim 1, wherein said first electrode contains an ionomeric binder which is the same substance as said ionomeric electrolyte.

11. The improvement of claim 10, wherein said ionomeric binder is a polymeric perfluoro sulfonated cation exchange membrane.

* * * * *